United States Patent [19]

Lobodzinski et al.

[11] Patent Number: 5,078,688
[45] Date of Patent: Jan. 7, 1992

[54] PARACENTESIS CATHETER SYSTEM

[75] Inventors: Richard Lobodzinski, Sunland; Peter D. Boasberg, Los Angeles, both of Calif.

[73] Assignee: Baxter International Inc., Deerfield, Ill.

[21] Appl. No.: 708,791

[22] Filed: May 28, 1991

Related U.S. Application Data

[63] Continuation of Ser. No. 411,343, Sep. 22, 1989, abandoned.

[51] Int. Cl.⁵ .............................................. A61M 25/00
[52] U.S. Cl. .................................. 604/164; 604/248; 604/317
[58] Field of Search ............ 604/32, 53, 164–169, 604/246, 248, 317, 322, 326

[56] References Cited

U.S. PATENT DOCUMENTS

| | | | |
|---|---|---|---|
| 2,485,842 | 10/1949 | Pennington | 604/248 |
| 2,842,124 | 7/1958 | James | 604/248 |
| 3,157,201 | 11/1964 | Littman | 604/32 |
| 3,276,472 | 10/1966 | Jinkens et al. | 604/248 |
| 3,459,184 | 8/1969 | Ring . | |
| 3,774,604 | 11/1973 | Danielsson . | |
| 3,853,127 | 12/1974 | Spademan . | |
| 3,875,938 | 4/1975 | Mellor . | |
| 3,934,576 | 1/1976 | Danielsson . | |
| 3,977,400 | 8/1976 | Moorehead . | |
| 4,000,739 | 1/1977 | Stevens . | |
| 4,073,297 | 2/1978 | Kopp . | |
| 4,252,122 | 2/1981 | Halvorsen | 604/164 |
| 4,447,235 | 5/1984 | Clarke . | |
| 4,496,348 | 1/1985 | Genese et al. . | |
| 4,531,935 | 7/1985 | Berryessa . | |
| 4,540,411 | 9/1985 | Bodicky | 604/169 |
| 4,566,480 | 1/1986 | Parham . | |
| 4,585,435 | 4/1986 | Vaillancourt | 604/83 |
| 4,626,245 | 12/1986 | Weinstein | 604/167 |

FOREIGN PATENT DOCUMENTS

| | | |
|---|---|---|
| 7734406 | 6/1978 | France . |
| 1026119 | 4/1966 | United Kingdom . |
| 2192793A | 1/1988 | United Kingdom . |

*Primary Examiner*—Stephen C. Pellegrino
*Assistant Examiner*—Ralph H. Lewis
*Attorney, Agent, or Firm*—Kay H. Pierce; Paul C. Flattery

[57] ABSTRACT

A paracentesis catheter system for removing fluids from a patient's abdominal cavity and for administering medication into the abdominal cavity. The catheter system includes a solid stylet, a catheter, a hemostasis valve assembly connected to the catheter, and delivery tubing with a needle connecting the catheter assembly to a stopcock. The stopcock has provisions for connections alternately to a syringe or to a vacuum bottle or drainage bag. The hemostasis valve includes an internal glan, which is compressed to shut off fluid flow through the end of the valve assembly after removing the solid stylet. This causes fluid to be diverted through the side arm tubing and stopcock to a fluid collection container.

1 Claim, 3 Drawing Sheets

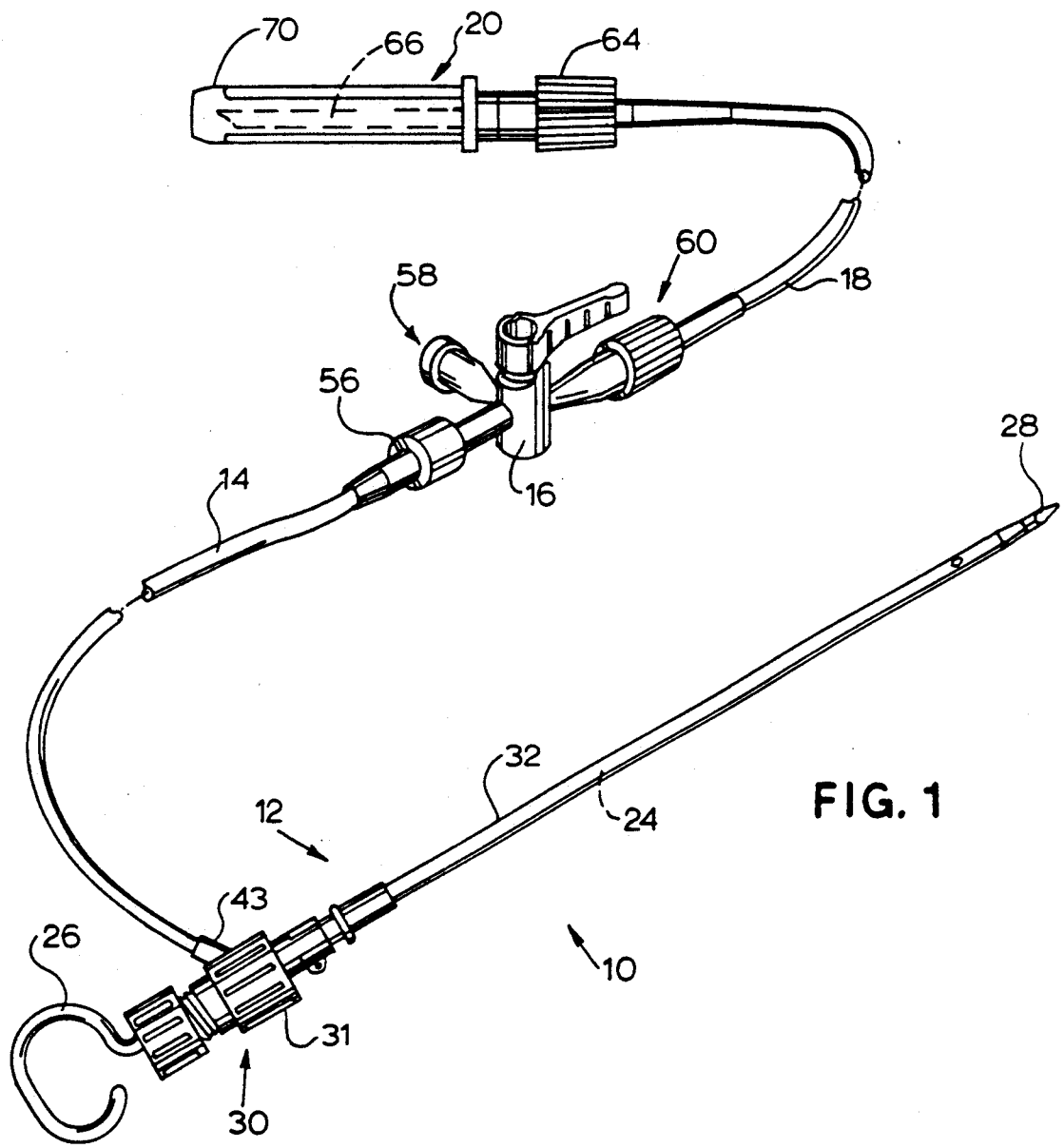
FIG. 1
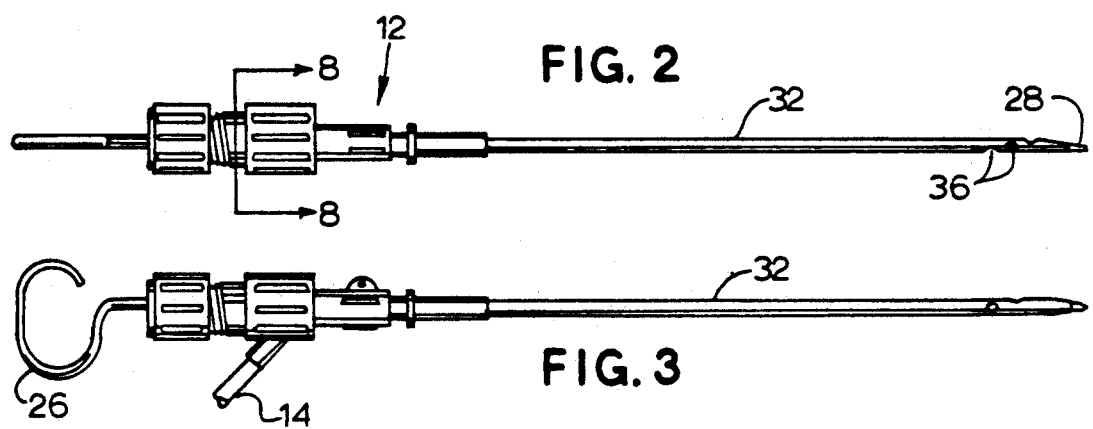
FIG. 2
FIG. 3

PARACENTESIS CATHETER SYSTEM

This is a continuation of application Ser. No. 07/411,343, filed Sept. 22, 1989, now abandoned.

BACKGROUND OF THE INVENTION

This invention relates to a paracentesis catheter system for removing fluids from the abdominal cavity and also for administering medication into the abdominal cavity.

There are numerous conditions which frequently cause fluids to collect in a patient's abdomen. One of these diseases, ascitis, is caused by a malignancies of the abdominal cavity and liver as well as various forms of liver diseases like liver cirrhosis. Collected ascitic fluid distends the abdominal cavity, causing local discomfort and shortness of breath. This fluid must be removed for both diagnostic and therapeutic purposes. The administration of medication into the abdominal cavity may follow the ascitic fluid drainage. Chemotherapy treatment or biologic response modifiers may be administered through the paracentesis catheter system to help management of malignancies.

In the past, the fluid has been removed by using trocar needle with catheters or catheter systems that are custom prepared for other medical procedures, such cathereter or catheter system include blood sets or catheters used for thoracentesis procedures.

Using the trocar needle, the medical personnel will first place a relatively large trocar needle in the patient and then thread a smaller catheter through the center of the needle. Either the needle must remain in the patient during the fluid draining procedure or else the needle can be. However, a removed trocar needle that is not removed will surround the portion of the catheter outside the body during the remainder of the procedure. The trocar needle is generally covered with body fluids and may expose hospital personnel to contaminated body fluids. Also the catheters used with the trocar needles are generally single hole catheters which can be easily occluded.

A blood donor set which has been used in the past for this procedure comprises a piece of tubing with a needle at each end and a roller clamp in the middle. This set is most often used with an evacuator bottle and requires that the sharp metal needle remain in the abdomen during the procedure. Because of the suction of the bottle, organs can be drawn to the sharp needle and can be damaged and/or also occlude the needle hole.

There are other drainage systems that are available either commercially or as assembled by hospital personnel. Generally they use a needle for insertion into the body cavity. These prior art systems allow for leakage of body fluids which may be undesirable in view of today's awareness of infectious diseases and the possibility of contamination by body fluids and the associated risks to hospital personnel. In addition, a needle cores skin and tissue when it is inserted into the patient, causing bleeding during and after the procedure. The end of the needle must be closed to prevent opening the body cavity to air. This increases the possibility of infection.

The paracentesis catheter system described herein is an improvement over the systems presently available because it provides a quick and efficient means to remove the fluid from the abdominal cavity and to provide a sample for diagnosis. This system also provides the advantage of substantially reducing or eliminating leakage of body fluids and also allows the administration of medication into the abdominal cavity.

SUMMARY OF THE INVENTION

This invention is directed to a system for draining fluids from a body cavity. It is discussed herein with regard to a paracentesis catheter assembly for draining fluid from a patient's abdominal cavity, but it has other medical applications as well such as administering medication, as discussed above.

The paracentesis catheter assembly comprises a tubing having a needle at one end and a catheter and stylet assembly at the other end. The tubing also has a three-way stopcock in the center. The fluid in the abdominal cavity can be drained into either a syringe, a vacuum bottle or a drainage bag, each of which may be alternately connected to one of the connections of the stopcock.

The stylet and catheter assembly includes a solid stylet with a ring at the end, a flexible catheter and a hemostasis valve. The hemostasis valve has an approximately cylindrical valve body and a nylon valve cap enclosing a silicon glan and two washers, one positioned on each side of the silicone glan.

The design present an advantage over earlier systems because it remains closed during the operating procedure, although it is open for a short time during the preparation for fluid withdrawal.

To withdraw fluid from a patient, the stylet is inserted into the hemostasis valve and catheter and is inserted into the abdomen of the patient. The stylet tip design allows for smooth penetration of the skin and abdominal muscles without tissue coring. This design is less traumatic and reduces post procedure leakage and bleeding. The solid stylet is removed and the valve cap is turned, forcing liquid to flow into the side arm of the valve body. Fluid flows from the side arm through the delivery tubing into the three-way stopcock which may be connected to various components. The side connection of the stopcock can be connected to a syringe. The end connection of the stopcock may be connected to either a vacuum bottle or to a drainage bag. The stopcock operates as a valve to direct and control the flow of fluid as is necessary according to the procedures selected.

DESCRIPTION OF THE DRAWINGS

FIG. 1 is a perspective view of the paracentesis catheter assembly.

FIG. 2 is a top view of the stylet/catheter assembly.

FIG. 3 is a side view of the stylet/catheter assembly.

DETAILED DESCRIPTION OF THE INVENTION

Figure 4:
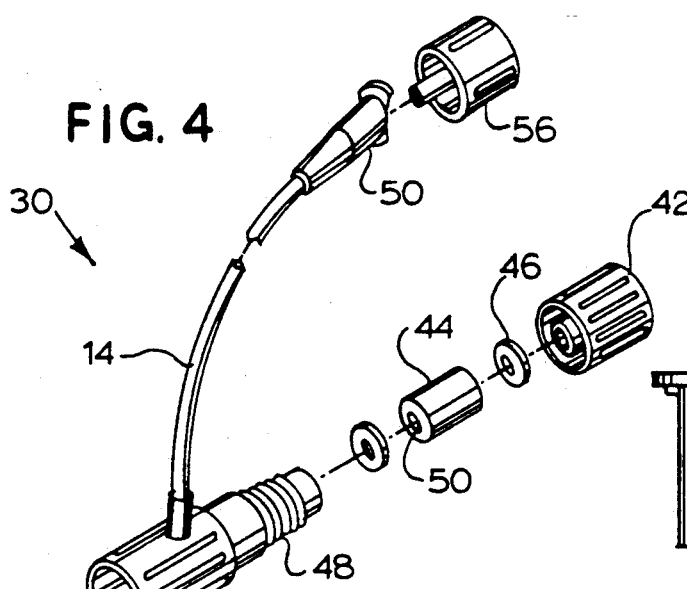
FIG. 4 is an exploded perspective view of a first embodiment of the hemostasis valve and side arm tubing.
Figure 5:
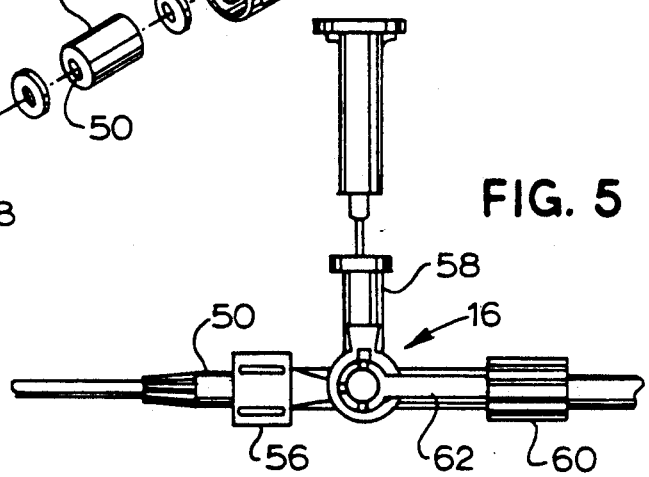
FIG. 5 is a top view of the stopcock connected to a syringe.
Figure 6:
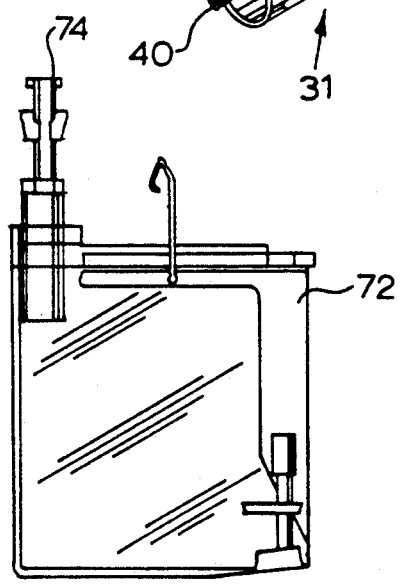
FIG. 6 is a front view of the needle and the drainage bag.
Figures 8, 9, 10:
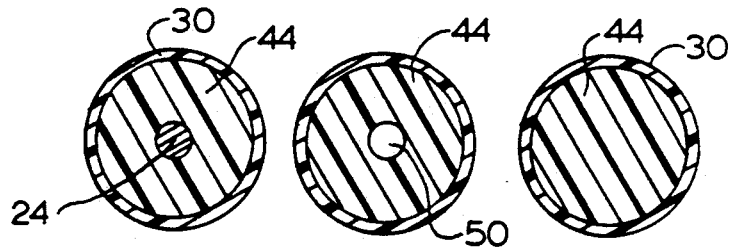
FIG. 8 is a cross-sectional view of the stylet/catheter assembly with the stylet in the catheter taken along lines 8—8 of FIG. 2.
FIG. 9 is a cross-sectional view of the stylet/catheter assembly with the stylet removed from the catheter taken along lines 8—8 of FIG. 2.
FIG. 10 is a cross-sectional view of the stylet/catheter assembly with the hemostasis valve closed taken along lines 8—8 of FIG. 2.
Figure 11A:
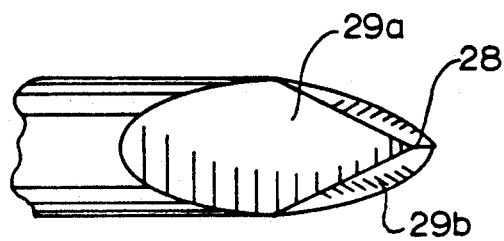
FIG. 11a is an enlarged top view of the stylet tip.
Figure 11B:
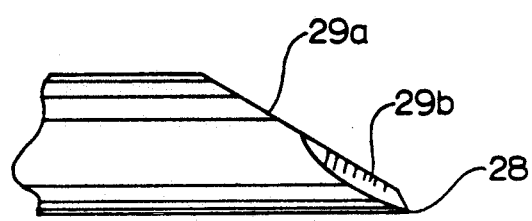
FIG. 11b is an enlarged side view of the stylet tip.
Figure 7:
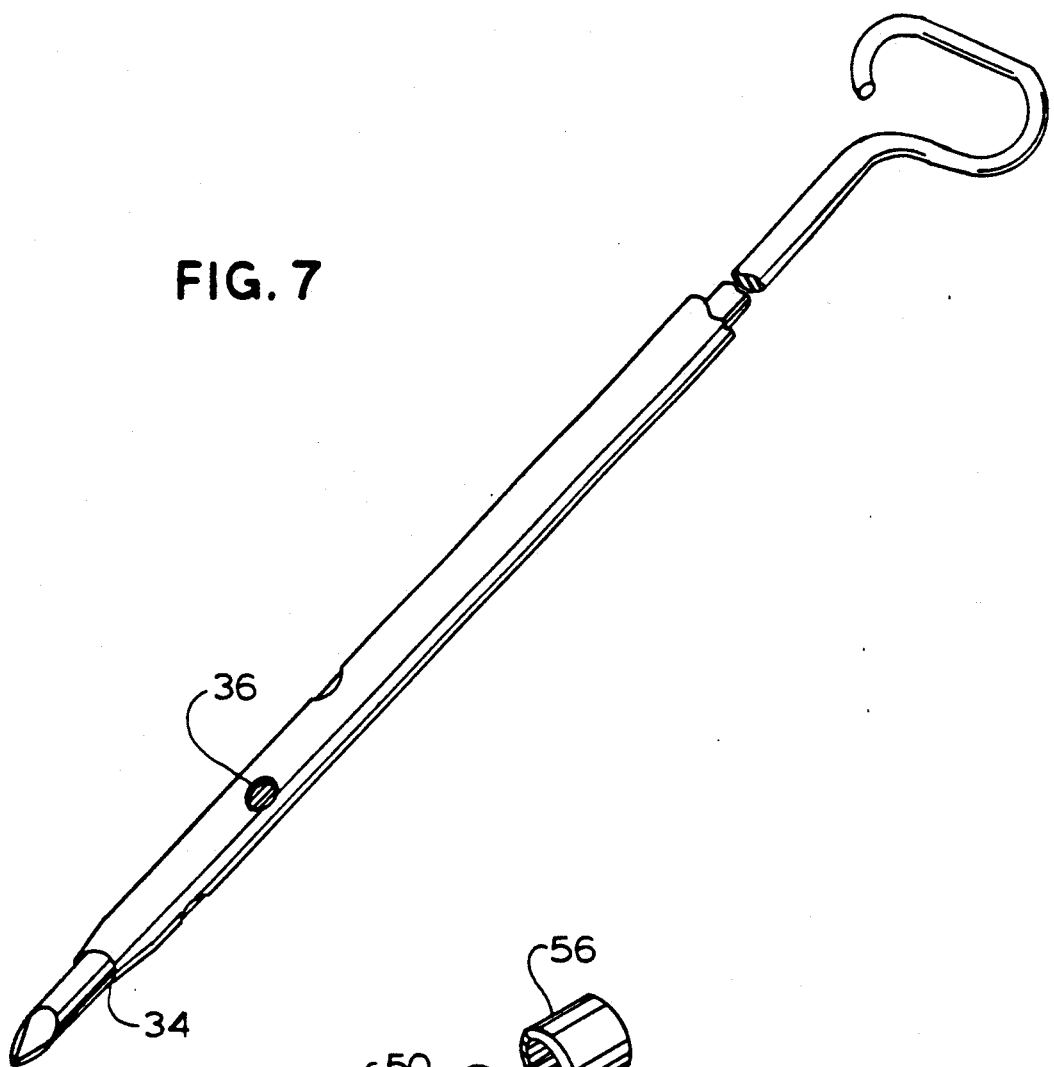
FIG. 7 is a perspective view of the catheter and stylet.

Referring to the drawings, and in particular to FIG. 1, the paracentesis catheter system is shown, generally indicated by numeral 10. The system includes a stylet and catheter assembly 12, side arm tubing 14, stopcock 16, delivery tubing 18 and needle assembly 20.

The stylet/catheter assembly 12 includes a solid stylet 24 with a sharpened point 28 at the proximal end and a ring 26 at the distal end. The sharpened point 28 includes a diagonal main surface 29a and beveled surfaces 29b.

Prior to beginning the procedure for draining the fluid from the body cavity, the stylet 24 must be positioned within the valve assembly 30 and flexible catheter 32 so that the stylet point 28 protrudes from the catheter end hole 34. Catheter 32 is formed of a relatively soft material and has an narrowed tip 33, both of which help to guide the catheter through the skin and abdominal muscles into the body cavity without injuring body organs. The catheter also has an end hole 34 and three side holes 36 which are located adjacent the end hole 34. The side holes 36 are distributed around the catheter with respect to one another both rotationally and longitudinally. For example, the three side holes 36 in the figures are distributed approximately 90/90/180 degrees with respect to one another and are also the longitudinally spaced from one another. Catheter 32 is hollow to form a first passageway.

A first preferred embodiment of valve assembly 30, as shown in FIG. 4, comprises valve body 31, valve cap 42, and a silicon glan 44 positioned between two nylon washers 46. Valve body 31 has at its proximal end an annular ridge 38 with internal threads and a central male luer fitting 39. The catheter has a hub 41 which is a female luer fitting with external threads to mate with the proximal end of the valve body. The distal end of the valve body 31 has external threads to mate with the internal threads of the valve cap 42.

The inner diameter of the valve body 30 and the outer diameter of the glan 44 are such that the glan 44 fits snugly within the valve body. The silicone glan 44 has a concentric opening 50, forming a third passageway, which is approximately equal to the diameter of the stylet 24. Thus the stylet fits snugly within the valve assembly 30.

After the stylet/catheter assembly 12 is used to pierce the abdominal wall of the patient and is inserted partially into the body cavity, the stylet 24 is removed leaving the catheter 32 to transmit the fluid. Because catheter 32 is made of a flexible material, body organs that are drawn to the tip of the catheter will not be injured. Even if body tissue clogs the tip of the catheter, the fluids will still be drawn into the system by the side holes 36.

After the stylet 24 is removed, the user twists the valve cap 42 clockwise. The valve cap 42 has inner threads that mate with the external threads 48 of the distal end of valve body 30, causing the valve cap 42 to compress the silicon glan 44 lengthwise. The glan 44, which is located within the limited diameter of the distal portion of the valve body 30, is compressed until the glan opening 50 is forced against itself so that it no longer passes fluid.

Figure 12:
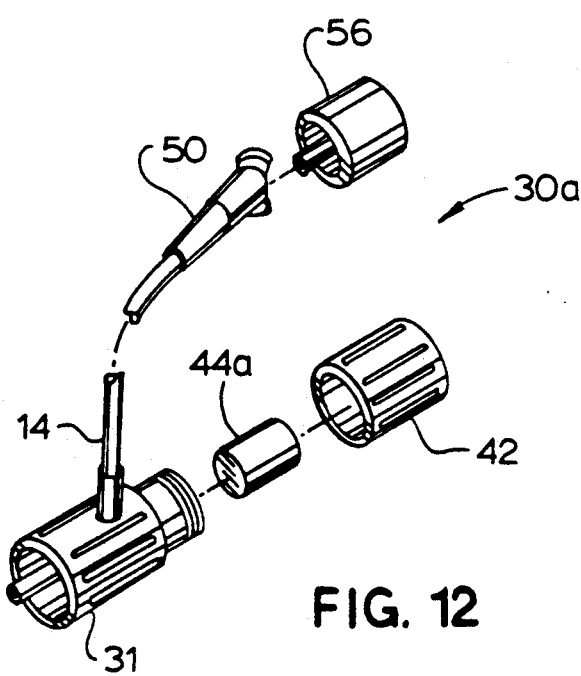
FIG. 12 is an exploded perspective view of a second embodiment of the hemostasis valve and side arm tubing.

A second preferred embodiment of valve assembly, generally identified as 30a in FIG. 12 comprises a valve body 31, valve cap 42 and a silicon glan 44a. Valve assembly 30 is substantially identical to valve assembly 30, except that glan 44a has no center opening 50 and no washers 46 are used. Valve cap 42 is bonded to valve body 31 to compress glan 44a. Valve cap 42 is then nonrotating.

Prior to using the assembly, the stylet is inserted into the stylet/catheter assembly 12, piercing glan 44a in the process. The assembly is then used as described above. When the stylet is removed from the catheter and valve body 31, the glan 44a automatically seals the opening made by the stylet, creating a closed system.

The valve body 31 has a side arm connection or third passageway 43 connecting it to the side arm tubing 14 which has a female luer fitting 50 at its end. Female luer fitting 50 is connected to the male luer fitting of the patient connection 56 of the three way stopcock 16. The stopcock 16 also has a syringe connection 58 and a delivery connection 60, which are to be connected to a fluid collection container, such as a syringe, bottle or drainage bag. The position of lever 62 controls the direction of the flow in the stopcock. When not in use the stopcock syringe connection 58 is closed by a nonvented cap protector (not shown).

When the lever 62 is moved to the patient connection 56, there is no flow of fluid from the patient to the syringe connection 58 or delivery connection 60. When the lever 62 is moved to the syringe connection 58, fluid flows directly from the patient through the side arm tubing 14, stopcock 16, delivery tubing 18, needle assembly 20 to the bag or evacuation bottle. When the lever 62 is in the delivery connection 60 position, the fluid may flow from the patient to a the syringe connected to the stopcock.

The needle assembly 20 includes connector 64 having a male luer fitting 65. The male luer may be connected to a hollow needle which may be inserted into an evacuator bottle or it may be connected directly to a fluid collection bag.

DESCRIPTION OF OPERATION

Prior to using a stylet/catheter assembly 12 with the first valve assembly as shown in FIG. 4, the user first ensures that the stylet point 28 extends beyond the catheter end hole 34 and that the stopcock lever 62 is turned toward the catheter so that no fluid will flow from the patient. The valve cap 42 should be turned so that the stylet is tightly fitted within the valve assembly 31.

The catheter/stylet assembly is placed partially through the abdominal wall, for example, so that the catheter and stylet are approximately 33% within the patient's body cavity. The stylet is then removed and the valve cap 42 is turned clockwise to close off the valve so that fluid flows from the stylet 24 to the delivery tubing 18. The catheter is then advanced the desired distance into the body cavity. Because the flexible catheter is advanced without the stylet, the catheter bends to reduce injury to internal organs.

The valve assembly shown in FIG. 12 is used much as described above except that the stylet must be forced through the glan 44a to be placed within the catheter.

When the stylet is removed from the valve assembly the glan will close automatically and the catheter is then advanced the desired distance into the body cavity.

To obtain a fluid sample, a protective nonvented cap (not shown) is removed from the stopcock syringe connection 58 and a syringe is connected to the syringe connection 58. The stopcock lever 62 must be turned toward the delivery connection 60 so that flow is from the catheter 32, through the delivery tube 18 and stopcock 16 to the syringe.

An alternative method is to collect the fluid in a vacuum bottle. The protective cap 70 is removed from the needle 66 and the needle is inserted into the rubber stopper of an evacuator bottle. The stopcock lever 62 is then turned towards the delivery connection 58 to allow fluid flow from the patient to the needle 66. The fluid may also be collected in a fluid collection bag 72 by removing needle 66 from the male luer connector and connecting the male connector to the female luer connector 74 of the fluid collection bag 72. The stopcock lever 62 remains turned towards the syringe connection 58.

After the drainage of ascitic fluid is completed, the syringe with medication can be attached to the syringe connection 58. The stopcock lever is then turned to the delivery connection 60 and medication is administered through catheter into the patient.

While the invention has particularly been shown and described with reference to a preferred embodiment it will be understood by those skilled in the art that variations in form, construction and arrangement may be made therein without departing from the spirit and scope of the invention. All such variations are intended to be covered in the appended claims.

We claim:

1. A system for draining fluids from a patient's abdominal cavity, comprising:
    side arm tubing (14) having first and second ends;
    delivery tubing (18) having first and second ends;
    a needle (66) connected to said first end of said delivery tubing;
    a catheter and style assembly (12) connected to said second end of said side arm tubing at said second end of said side arm tubing,
    said assembly including
        a flexible catheter (32) having first and second ends, said second end of said catheter having an end hole (34) and a plurality of side holes (36), said second end of said catheter being able to be inserted in the patient's abdominal cavity, said catheter having a hemostasis valve assembly (30) attached to said first end, said valve assembly having
            a valve body (31) having proximal and distal ends and a side arm connection (43) located between said proximal and distal ends, said side arm connection in fluid communication with said second end of said side arm tubing, said proximal end of said valve body being attached to said first end of said catheter,
            a valve cap (42) attached to said distal end of said valve body, and
            a silicon glan (44) positioned between said valve cap and said valve body, said glan being compressible lengthwise by said valve cap and said valve body between said valve cap and said valve body to prevent fluid flow therebetween;
        a solid stylet (24) having a sharpened point (28) at a proximal end thereof for piercing an abdominal wall of the patient, said stylet also having a ring (26) at a distal end thereof, said sharpened point of said first end of said stylet being able to be removably inserted through said valve cap, said glan, said valve body and said catheter so that said point protrudes from said end hole of said second end of said catheter and when said stylet is removed said glan (44) is compressed to close an opening left by the removal of said stylet to prevent fluid flow from between said valve body and said cap; and
    a three-way stopcock (16) having a patient connection (56), a syringe connection (58) and a delivery connection (60), said patient connection in fluid communication with said first end of said side-arm tubing, said syringe connection being capable of fluid communication with a syringe and said delivery connection connected to said second end of said delivery tubing and being capable of fluid communication with a fluid collection container, said three-way stopcock also including a lever (62) for controlling fluid flow direction through said stopcock, said lever being able to be positioned over each of said patient, syringe, and delivery connections, when said lever is positioned over said patient connection fluid is prevented from flowing through said stopcock, when said lever is positioned over said syringe connection fluid is allowed to flow through said stopcock between said patient and syringe connections, and when said lever is positioned over said delivery connection fluid is allowed to flow through said stopcock between said deliver and patient connections.

* * * * *